Figure 1:
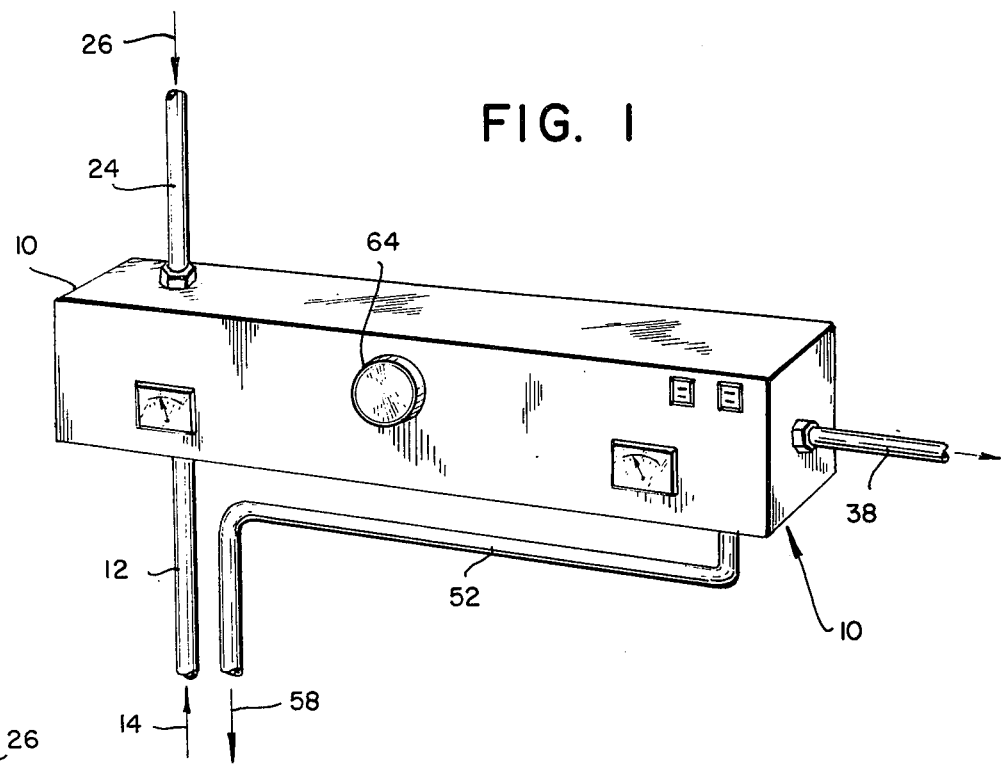

United States Patent [19]
Ellner

[11] 3,948,772
[45] Apr. 6, 1976

[54] SPLIT STREAM ULTRAVIOLET PURIFICATION DEVICE

[76] Inventor: Sidney Ellner, 6 Tudor Place, Hartsdale, N.Y. 10530

[22] Filed: Apr. 16, 1975

[21] Appl. No.: 568,660

[52] U.S. Cl............ 210/96 R; 21/102 R; 21/DIG. 2; 210/101
[51] Int. Cl.²......................................... B01D 21/24
[58] Field of Search............. 210/96, 101; 21/102 R, 21/DIG. 2

[56] References Cited
UNITED STATES PATENTS

| | | | |
|---|---|---|---|
| 3,443,691 | 5/1969 | Nilsson | 210/101 X |
| 3,682,305 | 8/1972 | Buchler | 210/96 X |
| 3,693,797 | 9/1972 | Todol | 210/96 |
| 3,825,494 | 7/1974 | Call et al | 21/102 R |

Primary Examiner—John Adee
Attorney, Agent, or Firm—Edward F. Levy

[57] ABSTRACT

A split stream ultraviolet purification device, for the treatment of liquids that are normally opaque to ultraviolet radiation, is provided with means for adding a selected amount of clear water to the inlet stream of untreated liquid entering a ultraviolet purification chamber. The clear water dilutes the opaque untreated liquid sufficiently to assure that the ultraviolet radiation level transmitted to the liquid flowing through the purification chamber is of a dosage high enough to effect complete disinfection. A control system regulates the flow of clear water to maintain a preselected level of ultraviolet radiation in the purification chamber and the control system diverts the discharge of the purification chamber to the source of untreated liquid in the event that the level of ultraviolet radiation in the purification chamber falls below the preselected level.

9 Claims, 2 Drawing Figures

U.S. Patent  April 6, 1976  3,948,772

SPLIT STREAM ULTRAVIOLET PURIFICATION DEVICE

The present invention relates in general to devices for the purification of liquids and more particularly to an ultraviolet purification device for the purification of sewage effluence and other opaque liquids.

Conventional ultraviolet purification devices comprise a purification chamber which houses a source of ultraviolet radiation, such as one or more ultraviolet lamps. Liquid to be treated is caused to flow continuously through the chamber, and as it flows it is subjected to ultraviolet radiation for purification. The chamber is provided with an ultraviolet sensing system including an ultraviolet sensor which is sensitive to radiation in the range of 2537 Angstrom and is located on the perimeter of the purification chamber. The ultraviolet radiation detected by the sensor is displayed on a meter, and in some instances the rate of flow of liquid through the chamber is automatically regulated in response to the level of radiation detected.

A major problem which limits the application of conventional ultraviolet purification devices is that when applied to extremely polluted sources, such as sewage effluence, fish hatchery effluence, wastes of pharmaceutical and food processing plants, and the like, the relatively high opacity of the fluid limits the transmission of the ultraviolet radiation and thus prevents the fluid from receiving a dosage of ultraviolet radiation high enough to destroy micro-organisms present. Where such opaque and polluted liquids are to be treated, the ultraviolet sensor detects such a small amount of radiation passing through the liquid that it decreases the rate of flow to such an extent as to render the system impractical. Thus conventional ultraviolet purification devices are found to be ineffective for fluids that are highly opaque to ultraviolet radiation.

It is an object of the present invention to provide an ultraviolet purification device which can be used to disinfect liquids which are normally opaque to ultraviolet radiation.

Another object of the present invention is to provide an ultraviolet purification device which guarantees that only liquid which has been properly disinfected will be discharged from the device.

Another object of the invention is to provide a split stream ultraviolet purification device which has a flow control valve to prevent an unanticipated increase in the flow of liquid through the device from resulting in an undesired decrease in the ultraviolet radiation dosage applied to the liquid.

Still another object of the invention the provision of a split stream ultraviolet purification device of the character described which can be used with conventional ultraviolet water purifiers to disinfect liquids that are normally opaque to ultraviolet radiation.

A further object of the invention is to provide a split stream ultraviolet purification device which is economical in manufacture.

In accordance with the present invention, there is provided a split stream ultraviolet purification device in which a selected amount of clear water is added to the inlet stream of opaque untreated liquid entering a ultraviolet purification chamber. The clear water dilutes the opaque untreated liquid sufficiently to assure that the ultraviolet radiation level transmitted within the purification chamber is of a dosage high enough to effect complete disinfection. The clear water is added to the inlet stream of opaque liquid by an electric mixing valve which is controlled by an ultraviolet monitoring system which receives a signal from an ultraviolet sensor located at the perimeter of the purification chamber. The electric mixing valve adjusts the flow of clear water in accordance with the requirements of the untreated liquid to maintain a predetermined level of ultraviolet radiation within the purification chamber.

The discharge pipe of the purification chamber leads to a flow control valve which limits the liquid flow to a preset rate, thus preventing an undesired decrease in the ultraviolet dosage received by the liquid in the purification chamber due to an increase in the flow rate of the untreated liquid. The discharge flows from the flow control valve to a solenoid valve, which is operated by the ultraviolet monitoring system, and which returns the liquid discharged from the purification chamber to the source of untreated liquid in the event that the entering liquid is so highly opaque that the addition of clear water does not render the mixture sufficiently transparent so as to receive the proper dosage of ultraviolet radiation for complete disinfection.

Figure 2:
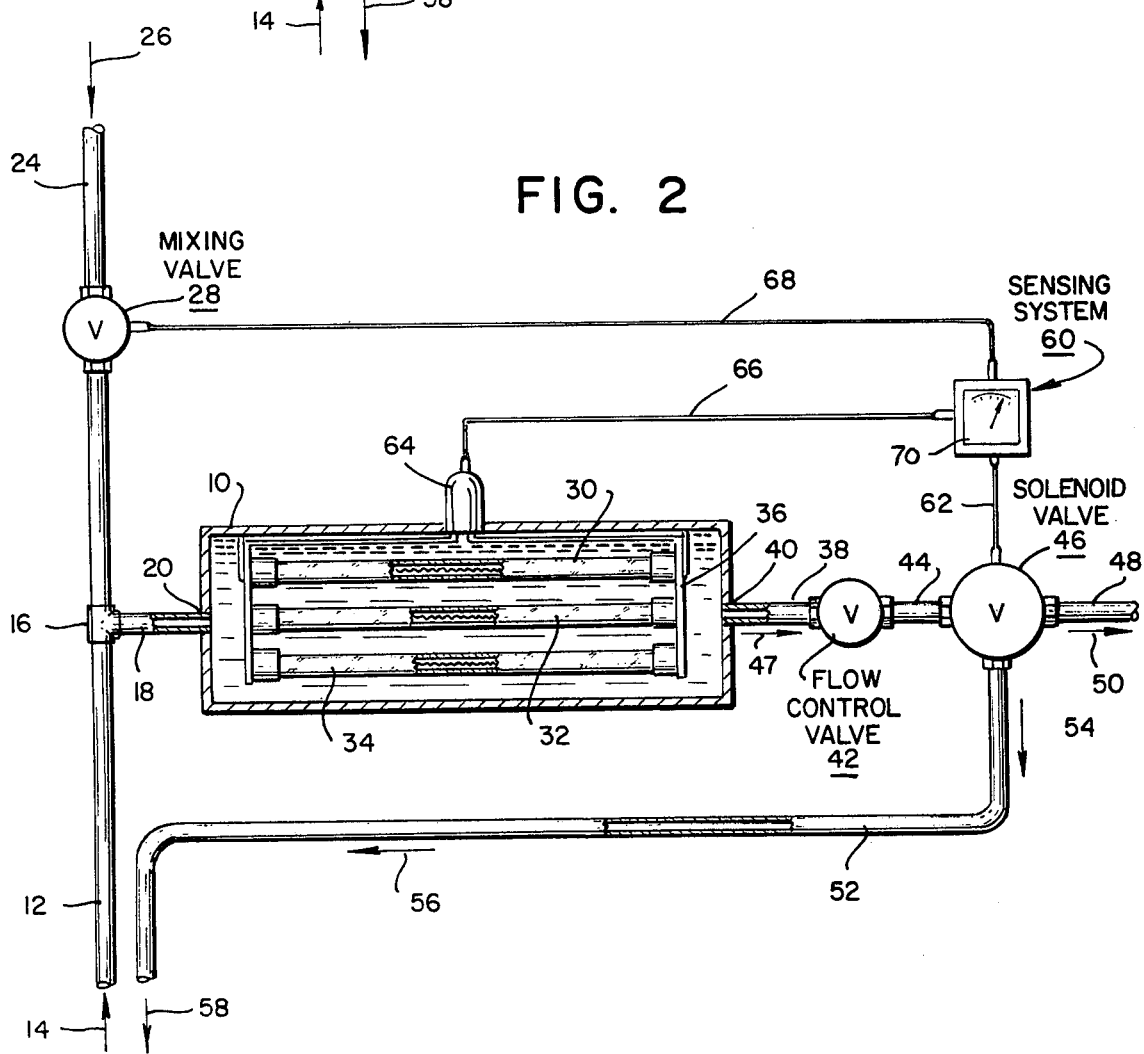

Additional objects and advantages of the invention will become apparent during the course of the following specification, when taken in connection with the accompanying drawings, in which:

FIG. 1 is an overall perspective view of a split stream ultraviolet purification device according to the present invention; and FIG. 2 is a schematic diagram illustrating a flow scheme for the split stream ultraviolet purification device of FIG. 1.

Referring in detail to the drawings, there is shown in FIGS. 1 and 2 a preferred embodiment of a split stream ultraviolet purification device made in accordance with the present invention. The split stream ultraviolet purification device includes a purification chamber 10 fed by an inlet pipe 12 through which sewage effluence or other untreated liquid flows into the chamber 10, in the direction of the arrow 14, from a source of untreated liquid, which is not shown. The inlet pipe 12 leads to a tee connection 16 from which mixing pipe 18 leads to the inlet 20 of the purification chamber 10.

A clear water inlet pipe 24 leads from a source of clear water to the tee connection 16. Clear water, fed to the split stream ultraviolet purification device, flows in the direction shown by the arrow 26 through the inlet pipe 24 to a mixing valve 28 which is mounted on the clear water inlet pipe 24. The clear water so fed dilutes the untreated liquid fed to the mixing pipe 18, prior to entering the purification chamber 10. The mixing valve 28, which may be either electrically or hydraulically operated, controls the flow of clear water in a manner which will be presently described.

The purification chamber 10 contains a source of radiation capable of producing ultraviolet radiation in the range of 2537 Angstroms. One such source of ultraviolet radiation, shown by way of example, is the set of ultraviolet lamps 30, 32 and 34, which are supported in a frame 36. The lamps 30, 32 and 34 are located at the center of the purification chamber 10.

An outlet pipe 38 leads from the discharge port 40 of the purification chamber 10 to a flow control valve 42 and a pipe 44 connects the flow control valve 42 to a solenoid valve 46. The direction of flow through pipe 38 is shown by the arrow 47.

The solenoid valve 46 directs the outlet flow of liquid either to a discharge pipe 48, through which properly disinfected liquid leaves the split stream ultraviolet purification device flowing in the direction shown by the arrow 50, or to a return pipe 52 which returns liquid to the source of untreated liquid, with the flow in this instance being in the direction shown by the arrows 54, 56 and 58 in FIG. 2. The action of the solenoid valve 46 is controlled by an ultraviolet monitoring system 60.

The solenoid valve 46 is connected to the ultraviolet monitoring system 60 via electrical lead connection 62. The ultraviolet monitoring system 60 is electrically connected by lead 66 to an ultraviolet sensor 64, which is mounted on the perimeter of the purification chamber 10. The ultraviolet monitoring system is also electrically connected to the mixing valve 28 by a lead 68.

The ultraviolet sensor 64 is preferably in the form of a conventional photo-electric cell capable of measuring the intensity of ultraviolet radiation which is received. The sensor 64 is mounted on a side wall of the purification chamber 10 where it receives ultraviolet rays emitted by the array of lamps 30, 32 and 34 at the center of the chamber and passing through the stream of liquid flowing through the chamber between the lamps and the sensor. If the intensity of the ultraviolet radiation received and measured by the sensor 64 is in the vicinity of 2537 Angstroms (or other designated level, depending on the type of liquid being treated), it signifies that all of the liquid flowing through the chamber is receiving the proper amount of ultraviolet radiation. In this instance, it is necessary to add only a very small amount of clear water or no clear water to dilute the liquid flowing through the purification chamber.

If the intensity of the ultraviolet radiation received and measured by the sensor 64 is below the designated level of radiation required to purify the liquid, it signifies that while the radiation received by the liquid flowing adjacent the lamps 30, 32 and 34 may be of the desired intensity, the liquid is too opaque to permit the radiation to penetrate through the entire extent of the liquid. Consequently, the flowing liquid in the vicinity of the side walls of the chamber is not receiving sufficient ultraviolet radiation for disinfectant treatment. In this situation, the sensor feeds this information to the monitoring system 60 which responds by opening mixing valve 28 to supply clear water for mixing with the liquid being treated, to such an extent that the designated radiation level is received by the sensor 64. If the effluent is too opaque to be sufficiently diluted by the clear water fed from inlet pipe 24, the monitoring system 60 functions to shut off the outlet flow of liquid through discharge pipe 48, and recirculates the liquid back to the liquid source through return pipe 52, and the liquid recirculates until it is sufficiently diluted to permit the passage of the ultraviolet radiation therethrough.

The ultraviolet monitoring system 60 contains electrical circuits which receive signals from the ultraviolet sensor 64 and compare these signals with a pre-set value of ultraviolet radiation, transmitting signals to the mixing valve 28 to adjust the flow of clear water to maintain the radiation level within the purification chamber 10 within acceptable limits of the pre-set value, and transmitting a signal to the solenoid valve 46 to divert the discharge flow from the purification chamber 10 to the return pipe 52 in the event that the radiation level in the purification chamber 10 falls below the pre-set acceptable limit.

The ultraviolet monitoring system 60 also includes a meter 70 displaying the level of the ultraviolet radiation in the purification chamber 22 and electrical output connections, which are not shown, for the connection of a strip chart recorder for continuously recording the level of the ultraviolet radiation in the purification chamber 22.

During operation, untreated liquid flows into the inlet pipe 12 and is mixed and diluted with clear water in the mixing pipe 18. The mixture flows into the purification chamber 10 and is subjected to ultraviolet radiation. The mixing valve 28 controls the flow of clear water in response to a signal from the ultraviolet monitoring system 60 in order to maintain the proper dilution of the liquid to maintain a pre-set level of ultraviolet radiation. The ultraviolet monitoring system 60 receives a continuous signal from the ultraviolet sensor 64 indicating the ultraviolet radiation level transmitted to the liquid with the purification chamber 10.

The total flow through the purification chamber is controlled by the fixed flow control valve 42 which assures that the rated capacity of the split stream ultraviolet purification device is never exceeded. The flow control valve 42 thus assures that the pre-set desired ultraviolet dosage is never decreased due to an inadvertant increase in the flow rate.

The solenoid valve 46 is controlled via an electrical signal from the ultraviolet monitoring system 60 and controls the flow of fluid discharged from the purification chamber 10. If the signal from the ultraviolet sensor 64 indicates that the ultraviolet radiation level is sufficiently high to effect complete disinfection of the liquid, then the liquid is discharged through discharge pipe 48. In the event that the mixing valve 28 is not capable of increasing the flow of clear water to such an extent as to dilute the untreated liquid sufficiently to achieve the proper level of ultraviolet radiation level, then ultraviolet monitoring system 60 will instantly sense this situation and will actuate the solenoid valve 46 to divert the flow from the purification chamber 22 to the return pipe 52. The split stream ultraviolet purification system 10 thus provides a fail-safe mode of operation and prevents the discharge of fluid which has not been properly disinfected.

While a preferred embodiment of the invention has been shown and described herein, it is obvious that numerous additions, changes and omissions may be made in such embodiments without departing from the spirit and scope of the invention.

What is claimed is:

1. An ultraviolet purification device comprising an ultraviolet purification chamber having a liquid inlet opening and a liquid outlet opening, a first inlet conduit for supplying opaque liquid to said inlet opening from a source of untreated liquid, a second inlet conduit for supplying clear liquid to said inlet opening, with said clear liquid mixing with and diluting said opaque liquid, metering valve means disposed within said second inlet conduit for controlling the flow of clear liquid to said chamber, a discharge conduit leading from the outlet opening of said purification chamber, means for producing ultraviolet radiation centrally located within said chamber, ultraviolet sensor means disposed in said purification chamber at one peripheral extremity thereof, and control means connected to said ultraviolet sensor means and operable in response to signals received from said sensor means for regulating said metering valve means to control the flow of clear liquid through said second inlet conduit into said chamber in accordance with the level of ultraviolet radiation sensed by said ultraviolet sensor, whereby clear liquid is fed to said chamber and mixed with said untreated liquid in proportion to the opacity of the liquid detected by said sensor means.

2. An ultraviolet purification device according to claim 1 which also includes a return conduit connecting said discharge conduit to said source of untreated liquid, second valve means disposed within said discharge conduit and return conduit and having a first operative position in which it blocks said discharge conduit and permits liquid to flow through said return conduit, said control means being operatively connected to said second valve means for bringing the latter to its second operative position when the ultraviolet radiation detected by said sensor means falls below a preselected level.

3. An ultraviolet purification device according to claim 1 in which said control means includes display means for displaying said level of ultraviolet radiation detected by said sensor means.

4. An ultraviolet purification device according to claim 1 in which said metering valve means comprises an electrically operated valve.

5. An ultraviolet purification device according to claim 2 in which said control means includes electrical connections leading from said sensor means to said control means, electrical connections leading from said control means to said metering valve means, and electrical connections leading from said control means to said second valve means.

6. An ultraviolet purification device according to claim 5 in which said second valve means comprises a solenoid valve.

7. An ultraviolet purification device according to claim 1 in which said means for producing ultraviolet radiation comprises a plurality of ultraviolet lamps.

8. An ultraviolet purification device according to claim 1 in which said first inlet conduit and said second inlet conduit are coupled to a mixing pipe leading to said liquid inlet opening, whereby said opaque liquid and said clear liquid are mixed in said liquid pipe before entering said purification chamber.

9. An ultraviolet purification chamber according to claim 2 in which said return conduit communicates with said discharge conduit at a point exteriorly of said purification chamber, and in which said second valve means is disposed at the junction of said return conduit and discharge conduit.

* * * * *